(12) United States Patent
Popoff et al.

(10) Patent No.: US 7,976,828 B2
(45) Date of Patent: *Jul. 12, 2011

(54) ANTIPERSPIRANT/DEODORANT COMPOSITION

(75) Inventors: Christine M. Popoff, Morganville, NJ (US); Diana Henao, Dover, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/670,472

(22) Filed: Feb. 2, 2007

(65) Prior Publication Data

US 2008/0187503 A1 Aug. 7, 2008

(51) Int. Cl.
*A61K 8/18* (2006.01)
*A61K 36/00* (2006.01)
*A61K 36/48* (2006.01)
*A61Q 15/00* (2006.01)

(52) U.S. Cl. .............. 424/65; 424/725; 424/757
(58) Field of Classification Search .......... None
See application file for complete search history.

(56) References Cited

U.S. PATENT DOCUMENTS

| | | | |
|---|---|---|---|
| 4,120,948 A | 10/1978 | Shelton | |
| 4,202,879 A | 5/1980 | Shelton | |
| 5,134,130 A * | 7/1992 | Shaw et al. | 514/78 |
| 5,271,934 A | 12/1993 | Goldberg et al. | |
| 5,487,887 A * | 1/1996 | Benfatto | 424/66 |
| 5,599,555 A | 2/1997 | El-Nokaly | |
| 5,726,163 A | 3/1998 | Fujii et al. | |
| 5,744,130 A | 4/1998 | Guskey et al. | |
| 5,846,520 A | 12/1998 | Guskey et al. | |
| 5,902,572 A | 5/1999 | Luebbe et al. | |
| 5,932,199 A | 8/1999 | Esser | |
| 6,007,799 A | 12/1999 | Lee et al. | |
| 6,048,518 A | 4/2000 | Bianchi et al. | |
| 6,086,887 A | 7/2000 | Parrott | |
| 6,099,827 A | 8/2000 | Esser | |
| 6,171,601 B1 | 1/2001 | Gardlik et al. | |
| 6,177,066 B1 | 1/2001 | Patuat et al. | |
| 6,221,345 B1 | 4/2001 | Esser | |
| 6,231,842 B1 | 5/2001 | Scavone et al. | |
| 6,352,688 B1 | 3/2002 | Scavone et al. | |
| 6,372,234 B1 | 4/2002 | Deckers et al. | |
| 6,372,235 B1 | 4/2002 | Livoreil et al. | |
| 6,375,938 B1 | 4/2002 | Clothier, Jr. et al. | |
| 6,383,476 B1 | 5/2002 | Scavone et al. | |
| 6,436,382 B1 | 8/2002 | Chopra et al. | |
| 6,485,716 B1 | 11/2002 | Fei et al. | |
| 6,503,491 B2 | 1/2003 | Guenin et al. | |
| 6,511,658 B2 | 1/2003 | Mattai et al. | |
| 6,534,045 B2 | 3/2003 | Mattai et al. | |
| 6,713,051 B2 | 3/2004 | Mayes et al. | |
| 6,797,020 B2 * | 9/2004 | Murphy | 44/275 |
| 6,849,251 B2 * | 2/2005 | Banowski et al. | 424/65 |
| 6,969,510 B2 * | 11/2005 | Holerca et al. | 424/65 |
| 7,105,691 B2 * | 9/2006 | Holerca et al. | 556/27 |
| 2003/0061760 A1 * | 4/2003 | Tao et al. | 44/275 |
| 2003/0206973 A1 | 11/2003 | Gale | |
| 2003/0207971 A1 | 11/2003 | Stuart et al. | |
| 2004/0120909 A1 | 6/2004 | Lee et al. | |
| 2004/0197281 A1 | 10/2004 | Walling et al. | |
| 2004/0204601 A1 * | 10/2004 | Holerca et al. | 556/56 |
| 2004/0234468 A1 | 11/2004 | Kerschner et al. | |
| 2005/0048013 A1 | 3/2005 | Diec et al. | |
| 2005/0281767 A1 | 12/2005 | Walling et al. | |
| 2005/0281851 A1 * | 12/2005 | Cap | 424/401 |
| 2005/0287069 A1 * | 12/2005 | Walling et al. | 424/9.1 |
| 2006/0018855 A1 | 1/2006 | Batista et al. | |
| 2006/0115441 A1 | 6/2006 | James et al. | |
| 2006/0134037 A1 * | 6/2006 | Cropper et al. | 424/66 |
| 2007/0009459 A1 | 1/2007 | Magnant et al. | |

FOREIGN PATENT DOCUMENTS

| | | | |
|---|---|---|---|
| DE | 19962878 A1 * | 6/2001 | |
| DE | 10007198 A1 * | 8/2001 | |
| EP | 1 005 853 | 7/2002 | |
| EP | 1529521 | 5/2005 | |
| JP | 62-111912 | 5/1987 | |
| JP | 62111912 * | 5/1987 | |
| JP | 62111912 A * | 5/1987 | |
| WO | WO 91/18588 | 12/1991 | |
| WO | WO 97/46246 | 12/1997 | |
| WO | WO99/11233 | 3/1999 | |
| WO | WO 01/39730 | 6/2001 | |
| WO | WO01/70185 | 9/2001 | |
| WO | WO 2005025523 * | 3/2005 | |

OTHER PUBLICATIONS

Noro et al., Evaluation of the emulsifying activity of saturated egg phosphatide hydrogenation for the O/W type emulsion. Yakugaki Zasshi 105 (7): 634-9, 1985.*
Grompone, Properties of vegetable oils modified by hydrogenation, interesterification and fractionation, Grasas y Aceites, (1992) vol. 43, No. 6, pp. 330-335.*
Salkovic-Petrisic et al, Excipient-related adverse drug reactions]. Nuspojave pomoc.nu.nih tvari u lijekovima, Pharmaca, (2002) vol. 40, No. 3-4, pp. 177-197.*
U.S. Appl. No. 10/571,488, filed Sep. 9, 2004 to Popoff et al.
"Oil yields and characteristics". Retrieved from www.journeytoforever.org on Jul. 14, 2006.
U.S. Appl. No. 11/670,481, filed Feb. 2, 2007 to Misner et al.
File History for U.S. Appl. No. 11/670,481.
U.S. Appl. No. 11/972,882, filed on Jan. 11, 2008.
International Search Report for PCT/US2008/051803.
International Search Report for PCT/US2008/051853.

* cited by examiner

*Primary Examiner* — Qiuwen Mi
(74) *Attorney, Agent, or Firm* — Michael F. Morgan

(57) ABSTRACT

A composition comprising at least one plant derived oil having a melting point of about −15 to about 38° C. in an amount of about 5% or less by weight; and at least one active chosen from antiperspirant actives and deodorant actives in an amount of about 0.5 to about 16% by weight of the composition on an active weight basis. The composition can be used as an antiperspirant and/or deodorant when applied to an axillary area of a person.

20 Claims, No Drawings

ANTIPERSPIRANT/DEODORANT COMPOSITION

BACKGROUND OF THE INVENTION

Antiperspirant and/or deodorant compositions are used to reduce the sweat in an axillary (underarm) region and/or to kill bacteria in this region to reduce or eliminate body odor caused by bacterial growth in this region. Antiperspirants/deodorants can be provided in many forms, such as a roll on, a gel, or as a solid stick. These compositions are applied to the axillary region, and they dry as the volatile carriers evaporate away to leave the active material. When roll on or gel compositions dry, they can leave the skin feeling tacky with a wet feeling.

It would be desirable to provide an antiperspirant/deodorant composition that reduces or eliminates the tacky and or wet feeling, and in particular for roll-on applications where the water content is usually more than 50% of the formula.

BRIEF SUMMARY OF THE INVENTION

A composition comprising:
a) at least one plant derived oil having a melting point of about −15 to about 38° C. in an amount of about 5% or less by weight; and
b) at least one active chosen from antiperspirant actives and deodorant actives in an amount of about 0.5 to about 22% by weight of the composition on an active weight basis.

DETAILED DESCRIPTION OF THE INVENTION

As used throughout, ranges are used as a shorthand for describing each and every value that is within the range. Any value within the range can be selected as the terminus of the range. References to amounts in percentages throughout this specification are based on the active weight of the material to the total weight of the composition, except for surfactants, which are based on as supplied.

The composition can be a liquid or a gel. In the liquid form, the composition can be formulated to be a roll on antiperspirant and/or deodorant. In the liquid form, the composition can be an oil in water emulsion or a water in oil emulsion. In one embodiment, the composition is an oil in water liquid emulsion. In gel form, the composition can be anhydrous or aqueous. The liquid can be contained in any roll on dispenser that has a ball for applying the composition to the surface of the skin.

In one embodiment, the composition excludes glycerin (glycerol), sorbitol, ethylene glycol, propylene glycol, sunflower oil, borage seed oil, and combinations thereof. When present in sufficient amounts, these materials increase the tackiness of the composition as well as product dry-down time. Also, addition of these components do not add structure to the composition.

The composition includes a plant derived oil having a melting point of about −15 to about 38° C., which is an oil that is obtained from a plant or is a synthetically manufactured equivalent. As used herein, the term oil includes materials that are defined as a liquid wax. For example, jojoba oil can be referred to as a liquid wax. The methyl and ethyl esters of plant derived oils are also included in the definition of a plant derived oil. This plant derived oil can provide structure to the composition. In one embodiment, this material is present in an amount of about 5% or less by weight of the composition. Levels much higher than 5% will give an oily/greasy feel to the composition and give an increased dry time. In one embodiment, the amount of plant derived oil is about 1 to about 3% by weight of the composition. Examples of the plant derived oil include, but are not limited to, soybean oil, jojoba oil, coconut oil, safflower oil, palm kernel oil, cottonseed oil, and pine nut oil. In certain embodiments, the plant derived oils are partially hydrogenated versions of theses oils. Lower levels of unsaturation can reduce potential chemical interaction with other roll-on components and can also reduces the tendency for the oil to oxidize and form a rancid odor that is harder to fragrance. The iodine value and percent saturates (which are inversely proportional to each other) are two means of describing the degree of hydrogenation present in the plant derived oil.

The presence of the plant derived oil reduces the tackiness of the antiperspirant active, which is found in the aqueous phase. The addition of optional emollients in combination with the plant derived oil can also give this desired effect when the total amount of emollient and the plant derived oil is about 5% or less. The tackiness is determined by an expert sensory panel comprised of at least 10 trained panelists who assess the skin feel properties of the formulas. One of the product characteristics measured in the test, both on forearm and axillary, is tackiness. The trained panelist assesses the tackiness of the product by feeling the product with her fingertips at given time intervals and rating the tackiness on a scale of 0 (no tack) to 10 (very tacky).

Ameliorating the wet feeling can also be achieved by providing some structure and body to the formula that the wearer perceives as providing a richness to the formula.

In one embodiment, the plant derived oil is selected to be partially hydrogenated and have a melting point that is about −15° C. (5° F.) to about 38° C. (100° F.). In another embodiment, the melting point is about 26° C. (80° F.) to about 35° C. (95° F.). To obtain the desired melting point, the plant derived oil can be partially hydrogenated or a blend of non-hydrogenated with partially or fully hydrogenated oils and/or waxes.

In one embodiment, the plant based oil comprises a partially hydrogenated soybean oil having an iodine value in the range of about 75 to about 80. Iodine value can be measured by ASTM D5554-95 (2006). This partially hydrogenated soybean oil can be obtained from Cargill under the product designation S-500. This material has a typical fatty acid distribution shown in the table below. Amounts shown are in % by weight.

| | |
|---|---|
| C16:0 | 10.5-11.2 |
| C18:0 | 6.8-7.5 |
| C18:1 | 61-65 |
| C18:2 | 16-19 |
| C18:3 | 0-0.2 |
| Saturates | 17.5-19.5 |
| Trans | 34-39 |

Another benefit of using a partially hydrogenated plant oil such as soybean oil is that it can provide structure, in the form of increased viscosity, to the composition. Viscosity or structure of a liquid composition is measured in mPas (centipoise) by a Brookfield Viscometer at 23° C. using spindle 4 at an RPM setting of 20. Viscosity of a gel composition is measured in Pa (G' and G") by an AR 1000 rheometer at 21° C. using an oscillatory mode.

An additional benefit of using a partially hydrogenated plant oil such as soybean oil within the present invention is the ease of fragrancing the composition. The reduced level of malodor formed during the aging of the composition when formulating with partially hydrogenated plant oils, allows for the fragrance to provide great fragrance hedonics without having to also cover the malodor. Partially hydrogenated plant oils have a lower iodine value, which corresponds to fewer double bonds. The reduced number of double bonds provides for a lower propensity for fragrance degradation.

Any surfactant that can be used in antiperspirant and/or deodorant compositions can be included. The surfactant can be included in any desired amount. In one embodiment, the amount of surfactant is about 2 to about 12% by weight of the composition. The amount in the composition is based on the as supplied material. In another embodiment, the amount of surfactant is about 3 to about 10% by weight. In one embodiment, when the composition is an oil in water roll-on formula, the amount of surfactant is about 2 to about 5%. In one embodiment, when the composition is a water in oil gel composition, the amount of surfactant is about 3 to about 10%. Examples of the surfactant include, but are not limited to, nonionic surfactants, silicone surfactants, and combinations thereof.

Nonionic surfactants that can be used include, but are not limited to, (a) sorbitan esters and ethoxylated sorbitan esters (for example PEG-20 sorbitan isostearate, sorbitan monolaurate, polysorbate-20, polysorbate-40, polysorbate-60, polysorbate-80); (b) ethoxylates (for example, Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10); (c) ethoxylated adducts (for example, PEG-25 stearate, glyceryl stearate and PEG-100 stearate); (d) PEG esters (for example, PEG-8 oleate, PEG-8 laurate, PEG-8 dilaurate, PEG-12 dilaurate, PEG-80 diisostearate, PEG-40 stearate); (e) propoxylates (for example, PPG-10 butanediol, PPG-50 oleyl ether, PPG-2-ceteareth-9, PPG-3-deceth-3, PPG-5-ceteth-20); (f) ethoxylated modified triglycerides (for example, PEG-20 corn glycerides, PEG-12 palm kernel glycerides); (g) alkylphenol aromatic ethoxylates (for example, dinonylphenol ethoxylate with 9 moles of EO, octylphenol ethoxylate with 20 moles of EO, octylphenol ethoxylate with 40 moles of EO); (h) block copolymers that are alkoxylated glycols having ethoxylated and propoxylated segments (for example, POLOXAMER™182 and 234, POLOXAMER™105 Benzoate, and MEROXAPOL™174); and combinations thereof. In one embodiment, the nonionic surfactant is selected so that it has an HLB (hydrophilic-lipophilic balance) value of 8-16 (more particularly 8-12).

In one embodiment, the nonionic surfactant is selected from ethoxylated non-ionic surfactants and propoxylated non-ionic surfactants. Example of these include, but are not limited to Steareth 2, Steareth 20, and Steareth 21. In an oil in water composition embodiment, a combination of 2 surfactants, one having an HLB value of about 2 to about 8 (such as Steareth 2) and the other having an HLB of about 9 to about 18 (such as Steareth 20 and 21), can be used.

Examples of silicone surfactants can be found in U.S. Pat. No. 6,485,716, which is incorporated herein by reference only for the listing of the silicone surfactants. Suitable silicone surfactants include silicone polyglucosides (for example, octyl dimethicone ethoxy glucoside) and silicone copolyols having an HLB value (hydrophilic lipophilic balance) ≦8. The HLB value may be measured in a variety of ways such as described in conventional references or found listed in tables of data recording such values. It is intended that any type of HLB measurement technique may be used.

In general, silicone copolyols include, but are not limited to, copolyols of the following Formulae I and II. Formula I materials may be represented by:

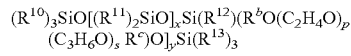

wherein each of $R^{10}$, $R^{11}$, $R^{12}$, and $R^{13}$ may be the same or different and each is chosen from C1-C6 alkyl; $R^b$ is the radical $—C_mH_{2m}—$; $R^c$ is a terminating radical which can be hydrogen, an alkyl group of one to six carbon atoms, an ester group such as acyl, or an aryl group such as phenyl; m has a value of two to eight; p and s have values such that the oxyalkylene segment $—(C_2H_4O)_p—(C_3H_6O)_s—$ has a molecular weight in the range of 200 to 5,000; the segment preferably having fifty to one hundred mole percent of oxyethylene units $—(C_2H_4O)_p—$ and one to fifty mole percent of oxypropylene units $—(C_3H_6O)_s—$; x has a value of 8 to 400; and y has a value of 2 to 40. Preferably each of $R^{10}$, $R^{11}$, $R^{12}$, and $R^{13}$ is a methyl group; $R^c$ is H; m is preferably three or four whereby the group $R^b$ is most preferably the radical $—(CH_2)_3—$; and the values of p and s are such as to provide a molecular weight of the oxyalkylene segment $—(C_2H_4O)_p—(C_3H_6O)_s—$ of between about 1,000 to 3,000. In one embodiment, p and s should each have a value of about 18 to 28. In one embodiment, the silicone copolyol is dimethicone copolyol.

A second siloxane polyether (copolyol) has the Formula II:

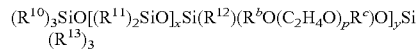

wherein p has a value of 6 to 16; x has a value of 6 to 100; and y has a value of 1 to 20 and the other moieties have the same definition as defined in Formula I.

It should be understood that in both Formulas I and II shown above, that the siloxane-oxyalkylene copolymers may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Thus, one or more of the $R^{10}$, $R^{11}$, $R^{12}$, and $R^{13}$ substituents that are attached to the two terminal silicon atoms at the end of the siloxane chain can be substituted with the segment $—R^b—O—(C_2H_4O)_p—(C_3H_6O)_s—R^c$ or with the segment $—R^b—O—(C_2H_4O)_p—R^c$. In some instances, it may be desirable to provide the segment $—R^b—O—(C_2H_4O)_p—(C_3H_6O)_s—R^c$ or the segment $—R^b—O—(C_2H_4O)_p—R^c$ at locations which are in the siloxane chain as well as at locations at one or both of the siloxane chain ends.

Particular examples of suitable dimethicone copolyols are available either commercially or experimentally from a variety of suppliers including Dow Corning Corporation, Midland, Mich.; General Electric Company, Waterford, N.Y.; Witco Corp., Greenwich, Conn.; and Goldschmidt Chemical Corporation, Hopewell, Va. Examples of specific products include DOW CORNING 5225C from Dow Corning, which is a 10% dimethicone copolyol in cyclomethicone; DOW CORNING 2-5185C, which is a 45-49% dimethicone copolyol in cyclomethicone; SILWET L-7622 from Witco; ABIL EM97 from Goldschmidt, which is a 85% dimethicone copolyol in D5 cyclomethicone; and various dimethicone copolyols available either commercially or in the literature.

It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone. The higher concentration materials such as DOW CORNING 2-5185 can be used in one embodiment.

In one embodiment, 0.5-5 weight % (particularly 1.0-2.0%) of a 10% silicone copolyol such as dimethicone copolyol in cyclomethicone mixture may be used, wherein the amount of mixture added is selected so that the level of silicone copolyol in the composition is in the range of 0.05-0.5% (particularly 0.1%) (for example, 1% of a 10% dimethicone copolyol in cyclomethicone mixture).

The composition can additionally include a betaine. The betaine of this invention is not a surfactant. Betaine in IUPAC nomenclature is 1-carboxy-N,N,N-trimethylmethanaminium hydroxide-inner salt, with alternative names including carboxymethyl-trimethyl-ammonium betaine or (carboxymethyl)trimethylammonium hydroxide-inner salt or glycine betaine or glycol betaine or glycyl betaine or trimethyl glycine or trimethylglycoll. For convenience here, the material of Formula A ($C_5H_{11}NO_2$; Mass=117.08 amu; molecular weight=117.15; analysis as C: 51.26; H: 9.46; N: 11.96; O: 27.32) will be referred to as Betaine.

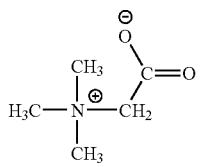

The hydrochloride form is also included in the scope of this invention. The hydrochloride form may be represented by Formula Aa, and it will be referred to as Betaine Hydrochloride:

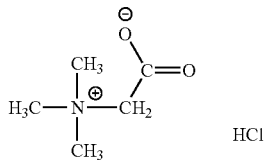

The use of betaine will refer to the Betaine of Formula A or the Betaine Hydrochloride of Formula Aa. More information about the betaine can be found in U.S. Pat. No. 6,969,510, which is incorporated herein by reference only for its disclosure of Betaine.

The betaine can be included in the composition in any desired amount. In one embodiment, the combined amount of plant oil and/or wax with betaine is about 10% by weight of the composition or less. In another embodiment, the combined amount is about 4 to about 8% by weight. In another embodiment, the weight ratio of betaine to plant oil and/or wax is 3:1 to 1:1.

The composition can additionally include ionizable inorganic salts. These ionizable salts are of the form $M_aX_b$ where a=1, or 2 and b=1 or 2; M is a member chosen from $Na^{+1}$, $Li^{+1}$, $K^{+1}$, $Mg^{+2}$, $Ca^{+2}$, $Sr^{+2}$, and $Zn^{+2}$ and X is a member chosen chloride, bromide, iodide, citrate, gluconate, lactate, glycinate, glutamate, ascorbate, aspartate, nitrate, phosphate, hydrogenphosphate, dihydrogenphosphate, formate, maloneate, maleate, succinate, carbonate, bicarbonate, sulfate, and hydrogensulfate. In certain embodiments, the selected salts are chosen from NaCl and $ZnCl_2$. As will be appreciated by those skilled in the art, while it may be possible under certain circumstances to add a salt directly to a portion of the mixture during manufacturing, it is desired to add the salt as a mixture or solution of the salt in a carrier or solvent, particularly water. Of course various concentrations of the salt premix can be made.

When the composition includes an antiperspirant active, any of the known antiperspirant active materials can be utilized in the composition. Antiperspirant actives include, but are not limited to, aluminum chlorhydrate, aluminum chloride, aluminum sesquichlorohydrate, aluminum-zirconium hydroxychlorides, complexes or adducts of the above-mentioned active ingredients with glycol, such as propylene glycol (for example, "Rehydrol" II from Reheis Chemical Co.), and combinations thereof. Known aluminum-zirconium salts in combination with neutral amino acids, such as glycine (e.g., aluminum-zirconium tetrachlorohydrex Gly) can also be used. Generally, any of the Category I active antiperspirant ingredients, listed in the Food and Drug Administration's Monograph on Antiperspirant Drug Products for overall-the-counter human use (Oct. 10, 1973) can be used.

In other embodiments, the antiperspirant active is an aluminum salt and/or an aluminum-zirconium salt, such as those described above, that are further stabilized by betaine and a calcium salt. More information about betaine and calcium salt stabilized antiperspirant salts can be found in U.S. Patent Application Publication No. 2006/0204463 to Tang et al., which is incorporated herein by reference only for the disclosure of the antiperspirant actives.

In other embodiments, the antiperspirant active, such as those described above, is selected to have a low metal to chloride ratio. Examples of these antiperspirant actives can be found in U.S. Pat. No. 6,375,937 to Chopra et al. and in U.S. Patent Application Publication No. 2004/0109833 to Tang et al., which are incorporated herein by reference only for their disclosure of the antiperspirant active.

In other embodiments, the type of salt of interest, an aluminum zirconium tetrasalt or octasalt free of glycine are used wherein aluminum zirconium salt is stabilized by Betaine and has a metal to chloride ratio of about 0.9:1 to about 1.3:1 (and in other embodiments of about 0.9:1 to about 1.2:1 or about 0.9:1 to about 1.1:1). For the tetrasalt, the Al/Zr atomic ratio can be about 3.2:1 to about 4.1:1.0 and the Betaine:zirconium mole ratio can be about 0.2:1 to about 3.0:1 (or in other embodiments of about 0.4:1 to about 1.5:1). Another salt that can be used is an aluminum chloride salt buffered by Betaine, wherein the salt has a metal to chloride ratio of 0.9:1 to 1.3:1 (and in other embodiments of about 0.9:1 to about 1.2:1 or about 0.9:1 to about 1.1:1). For the octasalt the Al/Zr atomic ratio is about 6.2:1 to about 10.0:1 and the Betaine:Zr mole ratio is about 0.2:1 to about 3.0:1 (or in other embodiments of about 0.4:1 to about 1.5:1). In one embodiment, in the case of a salt that contains zirconium, the Betaine is incorporated during the synthesis of the salt so as to maximize the stabilizing effect this ingredient has (especially on the zirconium species). Alternatively, it can be post added to a glycine-free salt along with additional active phase ingredients to form a Betaine stabilized active.

Examples of commercially available glycine-free low M:Cl ratio tetrasalts and octasalts include, but are not limited to, REZAL™ AZP 955 CPG and REZAL™ AZP 885 respectively (both from Reheis Chemical Company, Berkeley Heights, N.J.). A more detailed description of making such commercially available salts can be found for example, in U.S. Pat. Nos. 7,074,394 and 6,960,338. Further examples of making these types of salt complexes are described in U.S. Patent Application Publication No. 2004/0198998 and U.S. Pat. No. 7,105,691.

In addition to the anti-irritation properties of Betaine, it has also been found that antiperspirant formulations preserve their fragrance stability upon ageing when the Al/Zr salt is used in association with Betaine.

Additionally, the antiperspirant active can be a calcium salt stabilized antiperspirant active. Examples of calcium salt stabilized antiperspirant actives can be found in U.S. Patent Application Publication No. 2006/0204463, which is incorporated herein by reference only for the disclosure of the calcium salt stabilized antiperspirant actives.

In addition, any new ingredient, not listed in the Monograph, such as aluminum nitratohydrate and its combination with zirconyl hydroxychlorides and nitrates, or aluminum-stannous chlorohydrates, can be incorporated as an antiperspirant active. Antiperspirant actives can include, but are not limited to, the following: astringent salt of aluminum, astringent salt of zirconium, aluminum bromohydrate, aluminum chlorohydrate, aluminum dichlorohydrate, aluminum sesquichlorohydrate, aluminum chlorohydrex PG, aluminum dichlorohydrex PG, aluminum sesquichlorohydrex PG, aluminum chlorohydrex PEG, aluminum dichlorohydrex PEG, aluminum sesquichlorohydrex PEG, aluminum chloride, aluminum sulfate, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorhydrex propylene glycol, aluminum zirconium trichlorohydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate. In one embodiment, the antiperspirant active is aluminum chlorhydrate. In another embodiment, the antiperspirant active is aluminum zirconium tetrachlorhydrex propylene glycol.

When the composition contains a deodorant active, any known deodorant active can be used. Examples of deodorant active include, but are not limited to antimicrobial actives, alcohols, 2,4,4'-trichloro-2'-hydroxy diphenyl ether (Triclosan), octoxyglycerin (SENSIVA™ SC 50). benzethonium chloride, polyhexamethylene biguanides, triethylcitrate, 2-amino-2-methyl-1-propanol (AMP), cetyl-trimethylammonium bromide, cetyl pyridinium chloride, bactericides, and bacteriostats.

The composition may also contain particulates which include but are not limited to talc, mica, fragrance encapsulates, or hydrophobically modified starches, such as aluminum starch octenyl succinate (MACKADERM™ ASTRO-DRY™ from McIntyre Group Ltd.). If the composition is in a liquid form and dispensed through a roll-on applicator, the average particle size of the suspended material is sized so that it can pass through the application to prevent the ball applicator from malfunctioning. Usually, the average particle size does not exceed 150 microns.

In certain embodiments, the composition may also contain as an optional ingredient at least one malodor counteracting alpha, beta-unsaturated ester or mixtures of such materials. In certain embodiments, the level of malodor counteracting composition to deliver a perceivable odor control benefit when delivered from an antiperspirant and/or deodorant composition is about 0.05 to about 0.45 weight % based on the entire composition. The alpha, beta-unsaturated ester malodor counteracting materials are incorporated within the oil phase of an antiperspirant composition. Example of these malodor counteracting components can be found in U.S. Pat. No. 6,610,648 and U.S. Pat. No. 6,495,097, which are incorporated herein only for their disclosure of the alpha, beta unsaturated esters. For example, in this invention the odor neutralizing alpha, beta unsaturated ester mixture demonstrates unexpected stability in antiperspirant compositions containing low metal:chloride (M:Cl) ratio salts free of glycine. Examples of the alpha, beta unsaturated ester can be found in WO2005/025523, which was filed in the U.S. as U.S. application Ser. No. 10/571,488, both of which are incorporated herein by reference to the extent that they do not conflict with the disclosure in this specification.

Examples of the alpha, beta unsaturated ester include, but are not limited to:

(1) 3-phenyl-2-propenoic acid alkyl esters wherein $R^1$ is a substituent on the benzene ring and is chosen from an alkyl, an alkoxy, an aryl, or a substituted aryl. In certain embodiments, $R^1$ is chosen from H, a $C_1$ to $C_8$ alkyl, a $C_1$ to $C_8$ alkoxy, or an aryl; and $R^2$ is a subsistent group replacing the carboxylic acid hydrogen to form the ester where $R^2$ has greater than 6 carbon atoms, an aryl, or a substituted aryl group, in certain embodiments $R^2$ is a $C_6$ to $C_{12}$ alkyl or is a benzyl group; and (2) an ester of fumaric or maleic acid having linear ester carbon chains from 3-9 carbons, for example dihexyl fumarate;

(3) e-phenyl propenoic acid ester chosen from octyl methoxy cinnamate, phenylethyl cinnamate, benzyl cinnamate; and (4) an aliphatic unsaturated ester, such as dihexyl fumarate.

The composition can contain emollients in any desired amount to achieve a desired emollient effect. In one embodiment, the amount of emollients is up to about 6% by weight of the composition. In another embodiment, the amount is up to about 2%. Emollients are known in the art and are used to impart a soothing effect on the skin. Non-volatile emollients are preferable in the present invention. Classes of non-volatile emollients include non-silicone and silicone emollients. Non-volatile, non-silicone emollients include $C_{12-15}$ alkyl benzoate. The non-volatile silicone material can be a polyethersiloxane, polyalkyarylsiloxane or polyethersiloxane copolymer. An illustrative non-volatile silicone material in the present invention is phenyl trimethicone. Non-limiting examples of emollients can be found in U.S. Pat. No. 6,007,799. Examples include, but are not limited to, PPG-14 butyl ether, PPG-15 stearyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl) adipate), Di-(2-ethyl hexyl) succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide. In one embodiment, In one embodiment, the emollient is selected from linear silicones, cyclic silicones, hydrocarbons, polyhydroxy alcohols having more than 3 carbon atoms, liquid or solid polyalkyleneglycol ethers containing a polypropylene glycol (PPG) moiety and terminating in an alkyl ether, and combinations thereof. In another embodiment, the emollient is a volatile silicone having a flash point of 100° C. or less, such as cyclomethicone or trisiloxane. In another embodiment, the emollient is a nonvolatile silicone, such as dimethiconol or a longer chain dimethicone.

By volatile silicone material is meant a material that has a measurable vapor pressure at ambient temperature. For the volatile silicone portion, examples of volatile silicones (particularly silicones with a flash point of 100° C. or less at atmospheric pressure) include cyclomethicone (especially cyclopentasiloxane, also called "D5"), "hexamethyldisiloxane", and low viscosity dimethicone (for example, Dow Corning 200 fluid having a viscosity of 0.5-5 centistokes). Such volatile silicones include conventional cyclic and linear volatile silicones. Illustratively, and not by way of limitation, the volatile silicones are one or more members chosen from cyclic polydimethylsiloxanes such as those represented by Formula III:

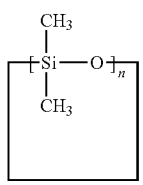
(III)

where n is an integer with a value of 3-7, particularly 5-6. For example, DC-245 fluid (or the DC-345 version) from Dow Corning Corporation (Midland, Mich.) is a type of cyclomethicone which can be used. These include a tetramer (or octylmethylcyclotetrasiloxane) and a pentamer (or decamethylcyclopentasiloxane). The volatile linear silicones can also be included in this group of volatile silicones and are one or more members chosen from linear polydimethylsiloxanes such as those represented by Formula IV:

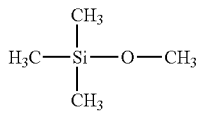
(IV)

which have a viscosity of 0.5-5 centistokes.

Examples of such volatile silicones include one or more members selected from D4, D5, and D6 cyclomethicones; and linear dimethicones having a viscosity in the range of 0.5-5 centistokes.

The composition may contain additional materials that are included in antiperspirant and/or deodorant compositions. Examples include, but are not limited to monohydric alcohols, fragrances, and preservatives.

When water is present, for example in a liquid roll-on composition, the amount of water in the composition is the amount to make a 100% by weight composition after all of the materials, including any optional materials, are added to the composition. In certain embodiments, the amount of water is at least about 20%, 30%, 40%, 50%, 60%, 70%, 80%, or 85% by weight of the composition.

The total solids of the composition is the amount of nonvolatile materials in the composition. The percent solids is measured by a CEM Smart System moisture/solids analyzer which uses microwave energy to dry the samples. In one embodiment, the total solids is less than about 25%. In another embodiment, the total solids is less than about 20%.

The invention is further described in the following examples. The examples are merely illustrative and do not in any way limit the scope of the invention as described and claimed.

Roll on liquid compositions can be prepared using the formulations and procedures given below.

Making Procedure

1. Aqueous Phase: Mix together DI Water & Surfactants:
   a. Heat Part 1 of water to 84-85° C.
   b. Melt and add to heated water the water phase surfactant (i.e. Steareth 20) Mix until solids are completely dissolved.
   c. Maintain temperature at 80-84 C.
2. Oil Phase: Mix together emollients and surfactant.
   a. Weigh out PPG 15.
   b. Melt oil phase surfactants (i.e. Steareth 2), add to PPG-15.
   c. Add emollients and plant derived oils un-melted.
   d. Add BHT
   e. Heat to 50° C. while mixing all the ingredients.
   f. Continue mixing, bring temperature to 64-66° C.
3. Using a **Rustin disk, add Oil phase to Aqueous phase under high shear mixing (360 rpm). Addition rate: approximately 20 g/min. Stop heating. Decrease mixing speed to 320 rpms.
4. When temperature drops to 68-70° C., add EDTA solution, continue mixing at 320 rpm.
5. Active Phase addition
   a. Increase mixing speed to 350 rpm, and slowly add part 2 of water—(cool).
   b. Add antiperspirant active ingredient, continue mixing at 350 rpm.
   c. Let temperature drop to 44-46° C.
   d. Slow down mixing speed to 320 rpms. Add Quaternium 15 solution.
   e. When temperature is 35° C. or below, slowly add fragrance using a dropper, continue mixing at 320 rpm.
   f. Continue mixing for additional 10-15 minutes after addition of fragrance is complete.

Alternatively, a homogenization step can be incorporated between steps 3 and 4. Using a Silverson homogenizer, homogenize for 5 minutes after addition of the oil phase is complete.

Alternatively, the antiperspirant active solution can also be added along with the water and aqueous phase surfactants.

Viscosity is measured in mPas (centipoise) by using a Brookfield Viscometer at 23° C. with spindle 4 at an RPM setting of 20.

All amounts shown in the examples below are % by weight based on the active weight of the material except for surfactants, which are based on as supplied. The amount for EDTA tetrasodium tetrahydrate includes the weight of the hydrate. EDTA is a 80%, so active weight is 0.2 weight %.

|  | 1 | 2 | 3 | 4 | 5 | 6 | 7 | 8 | 9 |
|---|---|---|---|---|---|---|---|---|---|
| Water | QS | QS | QS | QS | QS | QS | QS | QS | QS |
| Steareth 20 | 0.6 | 0.6 | 0.6 | 0.6 | 0.6 | 0.6 | 0.6 | 0.6 | 0.6 |
| Steareth 21 | 0.6 | 0.6 | 0.6 | 0.6 | 0.6 | 0.6 | 0.6 | 0.6 | 0.6 |
| PPG-15 Stearyl ether | 1.56 | 1.56 | 1.56 | 1.56 | 1.56 | 1.56 | 1.56 | 1.56 | 1.56 |
| Steareth-2 | 2.3 | 2.3 | 2.3 | 2.3 | 2.3 | 2.3 | 2.3 | 2.3 | 2.3 |
| Isopropyl palmitate | 1 | 0 | 0 | 0 | 0 | 0 | 0 | 0 | 0 |
| VARIONIC ™ APM-PPG 3 myristyl alcohol | 0 | 0 | 0 | 0 | 0 | 1 | 0 | 0 | 0.75 |
| Cyclopentasiloxane(DC245-Dow Corning) | 0 | 0 | 0 | 0 | 0 | 0 | 1.5 | 1.5 | 0 |
| Partially hydrogenated Soybean oil S500 (Cargill) | 2.0 | 0.0 | 2.0 | 0.0 | 2.0 | 1.0 | 1.5 | 0.0 | 0.0 |
| Non hydrogenated soy S100 (Cargill) | 0 | 2.0 | 0.0 | 2.0 | 0 | 0.0 | 0.0 | 1.0 | 1.0 |
| EDTA tetrasodium tetrahydrate | 0.25 | 0.25 | 0.25 | 0.25 | 0.25 | 0.25 | 0.25 | 0.25 | 0.25 |
| Di-tert. Butyl para cresol | 0.05 | 0.05 | 0.05 | 0.05 | 0.05 | 0.05 | 0.05 | 0.05 | 0.05 |
| Quaternium-15 | 0.1 | 0.1 | 0.1 | 0.1 | 0.1 | 0.1 | 0.1 | 0.1 | 0.1 |
| Aluminum Chlorohydrate Anhydrous (LOCRON ™, Clariant) | 12.1 | 12.1 | 12.1 | 12.1 | 12.1 | 12.1 | 12.1 | 12.1 | 12.1 |
| CARBOWAX ™ polyethylene glycol 400NF | 0 | 1 | 1 | 0 | 0 | 0 | 0 | 0 | 0 |
| Fragrance | 1 | 1 | 1 | 1 | 1 | 1 | 1 | 1 | 1 |
| % OIL PHASE* | 6.91 | 5.91 | 5.91 | 5.91 | 5.91 | 5.91 | 6.91 | 6.41 | 5.66 |
| Viscosity mPas | 2670 | 2120 | 2340 | 1530 | 2115 | 1510 | 1550 | 1600 | 1700 |

|  | 10 | 11 | 12 | 13 | 14 | 15 | 16 | 17 |
|---|---|---|---|---|---|---|---|---|
| Water | QS | QS | QS | QS | QS | QS | QS | QS |
| Steareth 20 | 0.6 | 0.6 | 0.6 | 1.2 | 1.2 | 0.6 | 0.6 | 0.6 |
| Steareth 21 | 0.6 | 0.6 | 0.6 | 0 | 0 | 0.6 | 0.6 | 0.6 |
| PPG-15 Stearyl ether | 1.56 | 1.56 | 1.56 | 1.56 | 1.56 | 1.56 | 1.56 | 1.56 |
| Steareth-2 | 2.3 | 2.3 | 2.3 | 2.3 | 2.3 | 2.3 | 2.3 | 2.3 |
| Isopropyl palmitate | 0 | 0 | 0 | 0 | 0 | 0 | 0 | 0 |
| VARIONIC ™ APM-PPG 3 myristyl alcohol | 1.5 | 0 | 0 | 0 | 0 | 0 | 0 | 0 |
| Cyclopentasiloxane(DC245-Dow Corning) | 0 | 1.5 | 0 | 0 | 0 | 0 | 0 | 0 |
| Partially hydrogenated Soybean oil S500 (Cargill) | 0.0 | 0.0 | 4.5 | 3.0 | 0.0 | 0.0 | 0.75 | 1.0 |
| Non hydrogenated soy S100 (Cargill) | 1.5 | 1.5 | 0.0 | 0 | 0 | 4.5 | 0.0 | 0.0 |
| EDTA tetrasodium tetrahydrate | 0.25 | 0.25 | 0.25 | 0.25 | 0.25 | 0.25 | 0.25 | 0.25 |
| Di-tert. Butyl para cresol | 0.05 | 0.05 | 0.05 | 0.05 | 0.05 | 0.05 | 0.05 | 0.05 |
| Quaternium-15 | 0.1 | 0.1 | 0.1 | 0.1 | 0.1 | 0.1 | 0.1 | 0.1 |
| Aluminum Chlorohydrate Anhydrous (LOCRON ™, Clariant) | 12.1 | 12.1 | 12.1 | 12.1 | 12.1 | 12.1 | 12.1 | 12.1 |
| CARBOWAX ™ polyethylene glycol 400NF | 0 | 0 | 0 | 0 | 0 | 0 | 0 | 0 |
| Fragrance | 1 | 1 | 1 | 0.1 | 0.1 | 1 | 1 | 1 |
| % OIL PHASE* | 6.91 | 6.91 | 8.41 | 6.91 | 3.91 | 8.41 | 5.66 | 4.91 |
| Viscosity mPas | 1720 | 1670 | 2430 | 2500 | 200 | 1810 | 1800 | 2150 |

|  | 18 | 19 | 20 | 21 | 22 | 23 | 24 | 25 |
|---|---|---|---|---|---|---|---|---|
| Water | QS | QS | QS | QS | QS | QS | QS | QS |
| Steareth 20 | 0.6 | 0.6 | 0.6 | 0.6 | 0.6 | 0.6 | 0.6 | 0.6 |
| Steareth 21 | 0.6 | 0.6 | 0.6 | 0.6 | 0.6 | 0.6 | 0.6 | 0.6 |
| PPG-15 Stearyl ether | 1.56 | 1.56 | 1.56 | 1.56 | 1.56 | 1.56 | 0.75 | 1.56 |
| Steareth-2 | 2.3 | 2.3 | 2.3 | 2.3 | 2.3 | 2.3 | 2.3 | 2.3 |
| Isopropyl palmitate | 0 | 0 | 0 | 0 | 0 | 0 | 0 | 0 |
| VARIONIC ™ APM-PPG 3 myristyl alcohol | 0 | 0 | 0 | 0 | 0 | 0 | 0 | 0 |
| Cyclopentasiloxane(DC245-Dow Corning) | 0 | 4.5 | 0 | 0 | 0 | 0 | 0 | 0 |
| Partially hydrogenated Soybean oil S500 (Cargill) | 2.0 | 0 | 0 | 0 | 3 | 1.0 | 2.0 | 3 |
| Non hydrogenated soy S100 (Cargill) | 0.0 | 0 | 4.5 | 3 | 0 | 0.0 | 0.0 | 0 |
| EDTA tetrasodium tetrahydrate | 0.25 | 0.25 | 0.25 | 0.25 | 0.25 | 0.25 | 0.25 | 0.25 |
| Di-tert. Butyl para cresol | 0.05 | 0.05 | 0.05 | 0.05 | 0.05 | 0.05 | 0.05 | 0.05 |
| Quaternium-15 | 0.1 | 0.1 | 0.1 | 0.1 | 0.1 | 0.1 | 0.1 | 0.1 |

-continued

| | | | | | | | | |
|---|---|---|---|---|---|---|---|---|
| Aluminum Chlorohydrate Anhydrous (LOCRON ™, Clariant) | 12.1 | 12.1 | 12.1 | 12.1 | 12 | 8 | 12.1 | 12 |
| CARBOWAX ™ polyethylene glycol 400NF | 0.5 | 0 | 0 | 0 | 0 | 0 | 0 | 0 |
| Fragrance | 1 | 1 | 1 | 1 | 1 | 1 | 1 | 1 |
| % OIL PHASE* | 5.91 | 8.41 | 8.45 | 6.91 | 6.91 | 4.91 | 5.10 | 6.91 |
| Viscosity mPas | 2400 | 1710 | 1880 | 1510 | 2170 | | 2000 | 2170 |

*The % oil phase is the total of the PPG-15 stearyl ether, Steareth-2, di-tert butyl para cresol, cyclopentasiloxane, and soybean oil.

In examples 1-25 above, the compositions that contained the plant derived oil had increased viscosity (increased structure) as compared to compositions that did not have the oil.

Additional examples are shown in the table below. They can be made using the methods described above.

| | 26 | 27 | 28 | 29 | 30 | 31 | 32 | 33 | 34 |
|---|---|---|---|---|---|---|---|---|---|
| Steareth-20 | 0.6 | 0.6 | 0.6 | 0.6 | 0.6 | 0.6 | 0.6 | 0.6 | 0.6 |
| Steareth-21 | 0.6 | 0.6 | 0.6 | 0.6 | 0.6 | 0.6 | 0.6 | 0.6 | 0.6 |
| Steareth-2 | 2.3 | 2.3 | 2.3 | 2.3 | 2.3 | 2.3 | 2.3 | 2.3 | 2.3 |
| PPG-15 stearyl ether | 1.56 | 1.56 | 1.6 | 1.6 | 1.56 | 1.56 | 1.56 | 1.56 | 1.0 |
| Cyclopentasiloxane (DC245 from Dow Corning) | 0 | 0 | 1.5 | 0 | 0 | 0 | 0 | 0 | 0 |
| PPG-3 myristyl ether | 0 | 0 | 0 | 0 | 0 | 0 | 0 | 0 | 0.6 |
| Aluminum starch octenyl succinate (ASTODRY ™-McIntyre) | 0 | 0 | 0 | 0 | 0 | 1.5 | 1.0 | 0 | |
| Jojoba oil | 0 | 0 | 3.5 | 0 | 0 | 0 | 0 | 0 | 0 |
| Soybean oil S100 (Cargill) | 3 | 1.5 | 0 | 3.0 | 1.5 | 0 | 0 | 0 | 1.5 |
| Soybean oil S500 (Cargill) | 0 | 0 | 0 | 0.0 | 0 | 1.0 | 1.0 | 3.0 | 0.0 |
| Hydrogenated polyisobutene FANCOL ™ Polyiso-200 | 0 | 0 | 0 | 0 | 0 | 0 | 0 | 0 | 1.5 |
| Isododecane (Permethyl 99A) | 1.5 | 0 | 0 | 0 | 0 | 0 | 0 | 0 | 0 |
| Diisopropyl Adipate (Ceraphyl 230) | 0 | 1.5 | 0 | 0 | 0 | 0 | 0 | 0 | 0 |
| Neopentyl glycol diheptonoate and isododecane LEXFEEL ™ D5 | 0 | 0 | 0 | 0 | 1.5 | 0 | 0 | 0 | 0 |
| Aluminum Chlorohydrate (anhydrous) (Locron, Clariant) | 12 | 12 | 12.5 | 12.5 | 12.5 | 12.0 | 12.0 | 12.0 | 12.5 |
| Water | QS | QS | QS | QS | QS | QS | QS | QS | QS |
| di-tertiary butyl-para-cresol | 0.05 | 0.05 | 0.05 | 0.05 | 0.05 | 0.05 | 0.05 | 0.05 | 0.05 |
| EDTA tetrasodium tetrahydrate | 0.25 | 0.25 | 0.25 | 0.25 | 0.25 | 0.25 | 0.25 | 0.25 | 0.25 |
| Quaternium 15 | 0.1 | 0.1 | 0.1 | 0.1 | 0.1 | 0.1 | 0.1 | 0.1 | 0.1 |
| Fragrance | 1 | 1 | 1 | 1 | 1 | 1 | 1 | 1.3 | 1 |
| odor neutralizing alpha, beta unsaturated ester mixture | | | | | | | | 0.2 | |
| Viscosity | 1240 | 990 | 1180 | 1510 | 960 | 1710 | 1680 | 2500 | 1140 |

The examples in the table below include betaine. They can be made using the methods described above.

| | 35 | 36 | 37 | 38 | 39 | 40 | 41 |
|---|---|---|---|---|---|---|---|
| Steareth-20 | 0.6 | 0.6 | 0.6 | 0.6 | 0.6 | 1.2 | 0.6 |
| Steareth-21 | 0.6 | 0.6 | 0.6 | 0.6 | 0.6 | 0.0 | 0.6 |
| Steareth-2 | 2.3 | 2.3 | 2.3 | 2.3 | 2.3 | 2.3 | 2.3 |
| PPG-15 stearyl ether | 1.56 | 1.56 | 1.56 | 1.56 | 1.56 | 1.56 | 1.56 |
| Cyclopentasiloxane (DC245 from Dow Corning) | 0 | 0 | 1.5 | 1.5 | 0 | 0 | 1.5 |
| Jojoba oil | 0 | 0 | 1.5 | 0 | 0 | 0 | 0 |
| Soybean oil S100 (Cargill) | 3.0 | 1.0 | 0 | 1 | 0 | 0 | 1 |
| Soybean oil S500 (Cargill) | 0 | 0 | 0 | 0 | 1.0 | 1.0 | 0 |
| Hydrogenated polyisobutene FANCOL ™ Polyiso-200 | 0 | 0 | 0 | 0 | 0 | 0 | 1.5 |
| Aluminum Zirconium tetrachlorohydrate (anhydrous) (Z498 - Summit) | 0 | 0 | 0 | 0 | 12.0 | 0 | 0 |

-continued

|  | 35 | 36 | 37 | 38 | 39 | 40 | 41 |
|---|---|---|---|---|---|---|---|
| Aluminum Chlorohydrate (anhydrous) (LOCRON ™ from Clariant) | 12.5 | 12.5 | 12.5 | 12.5 | 0 | 12.0 | 12.5 |
| Water | QS | QS | QS | QS | QS | QS | QS |
| di-tertiary butyl-para-cresol | 0.05 | 0.05 | 0.05 | 0.05 | 0.05 | 0.05 | 0.05 |
| EDTA tetrasodium tetrahydrate | 0.25 | 0.25 | 0.25 | 0.25 | 0.25 | 0.25 | 0.25 |
| Quaternium 15 | 0.1 | 0.1 | 0.1 | 0.1 | 0.1 | 0.1 | 0.1 |
| Fragrance | 1 | 1 | 1 | 1 | 1 | 1.0 | 1 |
| Trimethyl Glycine - Betaine | 3 | 3 | 3 | 3 | 0 | 0.0 | 3 |
| CaCl$_2$ (anhydrous) | 0 | 0 | 0 | 0 | 0 | 1.0 | 0.0 |
| Viscosity | 1780 | 2100 | 3160 | 1990 | 2200 | 1810 | 1560 |

The formula below provides an example of a water in oil gel composition that can be made using the following procedure. The sample sizes are about 500 grams. The silicone copolyol (PEG/PPG-18/18 dimethicone), silicones, soybean oil and fragrance are weighed and combined in a beaker. The mixture is stirred at 400-600 rpm using a Lightnin Mixer Model LI003. After the mixture becomes visually homogeneous, the active phase containing the antiperspirant active in water and the rest of the ingredients (tripropylene glycol, ethanol and additional water) are added to the oil phase while mixing. The entire mixture is mixed for 15 minutes. The mixture is then homogenized for 1-3 minutes at a reading of 40-60 on Powerstat Variable Transformer (Superior Electric Co., Bristol, Conn.) using a homogenizer from Greerco Corp. (Hudson, N.H.). A Brookfield viscometer with an E spindle and room temperature (about 23° C.) was used for determining the viscosity of these water in oil formulations. Note that the speed of an E spindle is 2.5 rpm

| Material | Amount |
|---|---|
| Cyclomethicone (DC345 from Dow Corning) | 6 |
| Phenyltrimethicone (DC556 from Dow Corning) | 1 |
| Dimethicone (DC200 from Dow Corning) | 2 |
| PEG/PPG-18/18 dimethicone in cyclopentasiloxane (DC5225C from Dow Corning-10% active) | 9 |
| Soybean oil S-500 (Cargill) | 1 |
| Aluminum Zirconium tetrachlorohydrex propylene glycol (Reheis 36 GPC) (active basis) | 16 |
| Tripropylene glycol | 3.3 |
| SD alcohol 40 | 8 |
| Fragrance | 0.7-1 |
| Water | QS |

What is claimed is:

1. A composition comprising:
   a. a structuring agent for the composition comprising a partially hydrogenated soybean oil with a melting point of about 26 to about 38° C. in an amount about 1% to of about 5% by weight;
   b. at least one active chosen from antiperspirant actives and deodorant actives in an amount of about 0.5 to about 16% by weight of the composition on an active weight basis;
   c. water in an amount that is at least 20% by weight of the composition to form a roll-on composition.

2. The composition of claim 1, wherein the composition excludes glycerin, ethylene glycol, propylene glycol, sorbitol, sunflower oil, borage seed oil, and combinations thereof.

3. The composition of claim 1, wherein the partially hydrogenated soybean oil has a melting point of 26 to 35° C.

4. The composition of claim 1 further comprising a surfactant.

5. The composition of claim 4, wherein the surfactant is present in an amount of about 2 to about 12% by weight of the composition.

6. The composition of claim 1, wherein an antiperspirant active is present.

7. The composition of claim 1, wherein an antiperspirant active is a glycine-free salt with a metal to chloride ratio of about 0.9:1 to about 1.3:1 and stabilized by betaine.

8. The composition of claim 7, wherein:
   (1) if the glycine-free salt is an aluminum and zirconium salt, then the metal/Cl ratio of the salt is about 0.9:1 to about 1.3:1; the betaine/Zr molar ratio is about 0.2:1 to about 3.0:1; and the betaine: aluminum molar ratio is about 0.05:1 to about 1.0:1;
   (2) if the glycine-free salt is only an aluminum salt, then the aluminuml/Cl molar ratio of the salt is about 0.5:1 to about 2.5:1; and the betaine/Al molar ratio is about 0.05:1 to about 1.0:1;
   (3) the pH of the glycine-free salt is about 2 to about 4 when measured in water at a concentration of 15%; and
   (4) the glycine-free salt is free of any halide scavenging material.

9. The composition of claim 1 further comprising betaine.

10. The composition of claim 9, wherein the betaine and the partially hydrogenated soybean oil are present together in an amount of about 10% or less by weight of the composition.

11. The composition of claim 9, wherein the betaine is present in the composition in a weight ratio of about 3:1 to about 1:1 based on the partially hydrogenated soybean oil.

12. The composition of claim 1 further comprising a particulate.

13. The composition of claim 12, wherein the particulate comprises a hydrophobically modified starch.

14. The composition of claim 1 further comprising an ionizable salt or combinations of ionizable salts of form $M_aX_b$ where a=1 or 2; b=1 or 2; M is a member chosen from $Na^{+1}$, $Li^{+1}$, $K^{+1}$, $Mg^{+2}$, $Sr^{+2}$ and $Zn^{+2}$, $Ca^{+2}$, and X is a member chosen from chloride, bromide, iodide, citrate, gluconate, lactate, glycinate, glutamate, ascorbate, aspartate, nitrate, phosphate, hydrogen phosphate, dihydrogen phosphate, formate, malonate, maleate, succinate, carbonate, bicarbonate, sulfate, and hydrogen sulfate.

15. The composition of claim 1 further comprising an emollient.

16. The composition of claim 1, wherein the composition is an oil in water liquid roll-on.

17. The composition of claim 1 further comprising an odor neutralizing alpha, beta unsaturated ester mixture.

18. The composition of claim 1, wherein the amount of water is at least 40% by weight of the composition.

19. The composition of claim 1, wherein the amount of water is at least 50% by weight of the composition.

20. A method comprising applying the composition of claim 1 to an axillary area of a person.

* * * * *